United States Patent
Heasman et al.

(10) Patent No.: US 11,305,109 B2
(45) Date of Patent: Apr. 19, 2022

(54) MONITORING STIMULATING ASSEMBLY INSERTION

(71) Applicant: Cochlear Limited, Macquarie University (AU)

(72) Inventors: John Michael Heasman, Hampton (AU); Peter Gibson, South Coogee (AU); Stephen O'Leary, Melbourne (AU); Luke Campbell, Melbourne (AU)

(73) Assignee: Cochlear Limited, Macquire University (AU)

( * ) Notice: Subject to any disclaimer, the term of this patent is extended or adjusted under 35 U.S.C. 154(b) by 0 days.

(21) Appl. No.: 16/703,926

(22) Filed: Dec. 5, 2019

(65) Prior Publication Data

US 2020/0215322 A1 Jul. 9, 2020

Related U.S. Application Data

(63) Continuation of application No. 15/245,547, filed on Aug. 24, 2016, now Pat. No. 10,500,392.

(51) Int. Cl.
| | |
|---|---|
| *A61N 1/05* | (2006.01) |
| *A61B 5/00* | (2006.01) |
| *A61N 1/36* | (2006.01) |
| *A61B 5/38* | (2021.01) |
| *A61B 5/12* | (2006.01) |
| *A61N 1/08* | (2006.01) |

(52) U.S. Cl.
CPC ............ *A61N 1/0541* (2013.01); *A61B 5/125* (2013.01); *A61B 5/38* (2021.01); *A61B 5/4851* (2013.01); *A61B 5/686* (2013.01); *A61N 1/08* (2013.01); *A61N 1/36036* (2017.08)

(58) Field of Classification Search
None
See application file for complete search history.

(56) References Cited

U.S. PATENT DOCUMENTS

| | | | |
|---|---|---|---|
| 5,419,312 | A | 5/1995 | Arenberg et al. |
| 5,776,179 | A | 7/1998 | Ren et al. |
| 6,640,121 | B1 | 10/2003 | Telischi et al. |
| 7,137,946 | B2 | 11/2006 | Waldmann |

(Continued)

FOREIGN PATENT DOCUMENTS

| | | |
|---|---|---|
| KR | 10-0859979 B1 | 9/2008 |
| WO | 2004022069 A1 | 3/2004 |

OTHER PUBLICATIONS

B. Escudé et al., "The Size of the Cochlea and Predictions of Insertion Depth Angles for Cochlear Implant Electrodes", Audiology & Neurotology 2006; 11(suppl 1):27-33, DOI: 10.1159/000095611, Oct. 6, 2006, 7 pages.

(Continued)

*Primary Examiner* — Erica S Lee
(74) *Attorney, Agent, or Firm* — Edell, Shapiro & Finnan, LLC

(57) ABSTRACT

Presented herein are techniques for monitoring the insertion of an intra-cochlear stimulating assembly for the occurrence of one or more insertion stop conditions. The insertion stop conditions are detectable events indicating that movement of the stimulating assembly into a recipient's cochlea should be at least temporarily stopped. The insertion monitoring is based on objectively measured inner ear potentials, such as acoustically-evoked potentials.

14 Claims, 9 Drawing Sheets

(56) References Cited

U.S. PATENT DOCUMENTS

| | | | |
|---|---|---|---|
| 8,086,319 | B2 | 12/2011 | van Dijk |
| 8,170,678 | B2 | 5/2012 | Polak |
| 8,554,330 | B2 | 10/2013 | Bradley et al. |
| 2005/0261748 | A1* | 11/2005 | van Dijk ............ A61N 1/36039 607/57 |
| 2009/0259140 | A1 | 10/2009 | Buchman et al. |
| 2011/0238176 | A1 | 9/2011 | Bradley et al. |
| 2012/0109006 | A1 | 5/2012 | James et al. |
| 2014/0066951 | A1 | 3/2014 | Llinas et al. |
| 2014/0247020 | A1* | 9/2014 | Stankovic ................. A61F 2/10 320/166 |
| 2014/0350640 | A1* | 11/2014 | Patrick ................. A61N 1/0541 607/57 |
| 2015/0057714 | A1 | 2/2015 | Litvak et al. |
| 2016/0059015 | A1* | 3/2016 | Risi .................... A61N 1/36038 607/57 |
| 2016/0217267 | A1* | 7/2016 | Kraus ...................... A61B 5/16 |
| 2018/0050196 | A1 | 2/2018 | Pawsey et al. |
| 2018/0304069 | A1* | 10/2018 | Koka .................. A61N 1/0541 |

OTHER PUBLICATIONS

Antje Aschendorff, "Imaging in cochlear implant patients", Laryngo-Rhino-Otologie, 90(S 01), S16-S21. doi:10.1055/s-0030-1270448, Review Article, GMS Currect Topics in Otorhinolaryngology—Head and Neck Surgery 2011, vol. 10, ISSN 1865-1011, 7 pages.

John A. Ferraro, "Electrocochleography: A Review of Recording Approaches, Clinical Applications, and New Findings in Adults and CHildren", J Am Acad Audiol 21:145-152 (2010), DOI: 10.3766/jaaa.21.3.2, Journal of the American Academy of Audiology, vol. 21, No. 3, 2010, 8 pages.

J. Xu et al., "Cochlear view: postoperative radiography for cochlear implantation", American Journal of Otolaryngology, 21(1), 49-56. doi:10.1016/S0196-0709(00)80075-7, OTOPUNS #1198, 9 pages.

International Search Report and Written Opinion in corresponding International Application No. PCT/IB2017/054948, dated Dec. 13, 2017, 11 pages.

Adunka et al., Monitoring of Cochlear Function During Cochlear Implantation, Laryngoscope 116, Jun. 2006, pp. 1017-1020.

\* cited by examiner

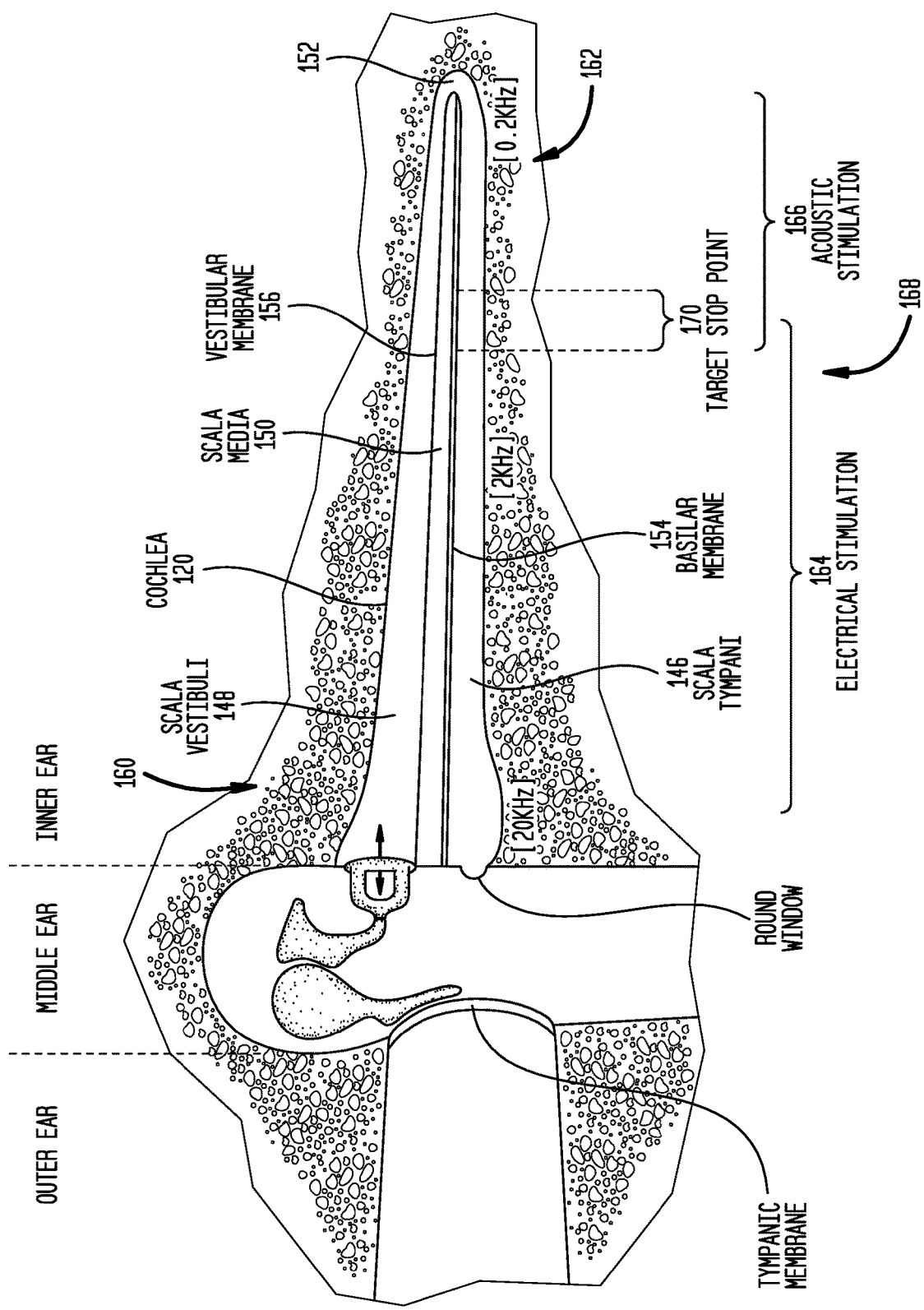

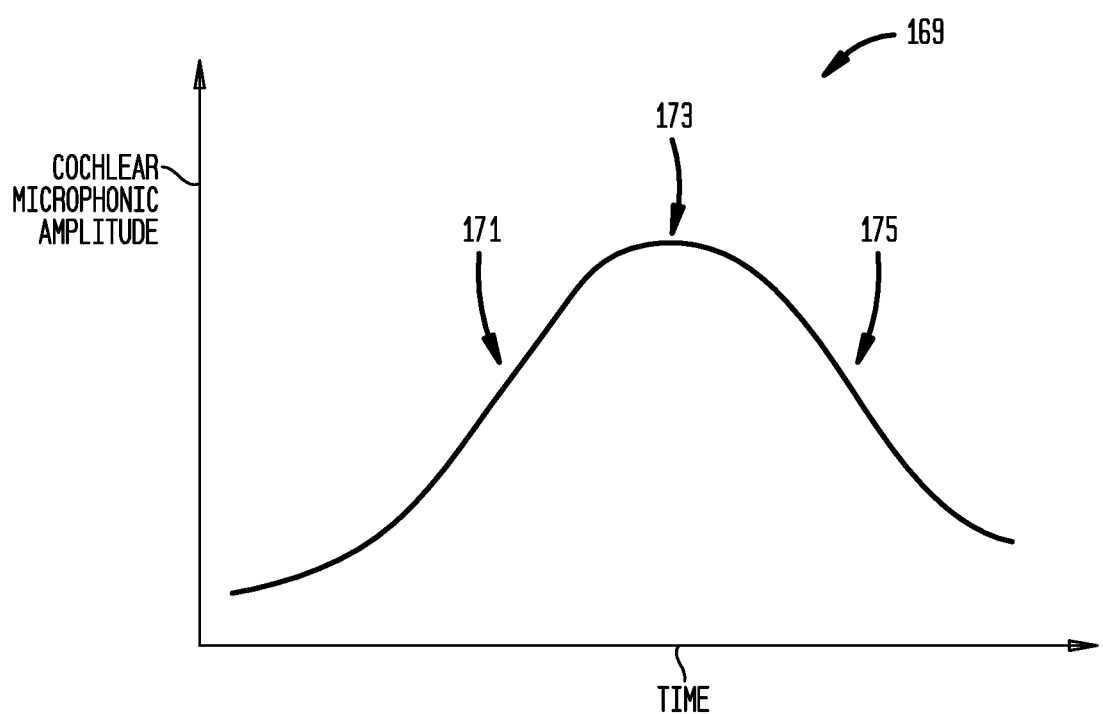

COCHLEAR MICROPHONIC TRACES

AMPLITUDE OVER TIME

COCHLEAR MICROPHONIC TRACES

AMPLITUDE OVER TIME

MONITORING STIMULATING ASSEMBLY INSERTION

CROSS-REFERENCE TO RELATED APPLICATION

This application is a continuation application of U.S. patent application Ser. No. 15/245,547, entitled "Monitoring Stimulating Assembly Insertion," which was filed on Aug. 24, 2016, and which issued as U.S. Pat. No. 10,500,392 on Dec. 10, 2019, the content of which is hereby incorporated by reference herein.

BACKGROUND

Field of the Invention

The present invention relates generally to insertion of implantable stimulating assemblies.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, a method is provided. The method comprises: during insertion of a stimulating assembly into a cochlea of a recipient, monitoring acoustically-evoked inner ear potentials obtained from the cochlea of the recipient; detecting, based on the acoustically-evoked inner ear potentials, an insertion stop condition; and responsive to detection of an insertion stop condition, initiating a feedback mechanism to stop insertion of the stimulating assembly into the cochlea.

In another aspect, a method is provided. The method comprises: determining an insertion stop condition for an electrode array of a cochlear implant for implantation in a recipient, wherein the insertion stop condition is based on a subjective measure of the recipient's residual hearing in the cochlea and an objective measure of the recipient's residual hearing in the cochlea.

In another aspect, a system is provided. The system comprises: a receiver configured to receive, from a cochlear implant during insertion of a stimulating assembly of the cochlear implant into the cochlea of a recipient, acoustically-evoked inner ear potentials, and a processor configured to detect from the acoustically-evoked inner ear potentials, an occurrence of an insertion stop condition, wherein the insertion stop condition is selected from the group comprising: an error stop condition comprising a change in the acoustically-evoked inner ear potentials indicative of a mechanical impedance change of the basilar membrane, and a target stop condition comprising a relative change in the acoustically-evoked inner ear potentials indicating that a one or more stimulating contacts of the stimulating assembly are located at a tonotopic position corresponding to a pre-operatively defined insertion stop frequency.

BRIEF DESCRIPTION OF THE DRAWINGS

Embodiments of the present invention are described herein in conjunction with the accompanying drawings, in which:

FIG. 2A is a diagram schematically illustrating a target stop point, in accordance with embodiments presented herein;

FIG. 2B is a graph illustrating measured cochlear microphonic amplitudes relative to time, in accordance with embodiments presented herein;

DETAILED DESCRIPTION

Figure 1A:
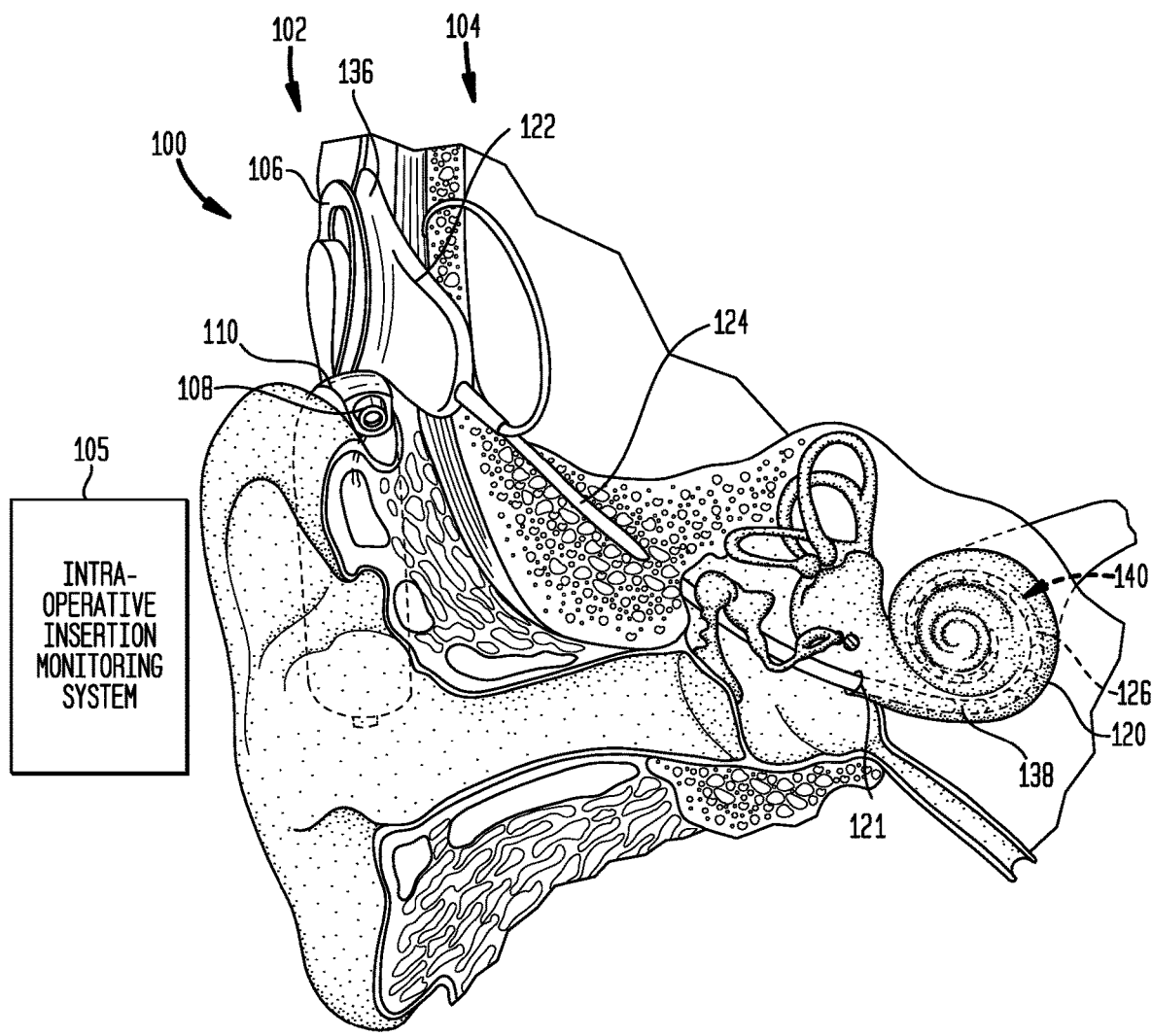
FIG. 1A is a schematic diagram illustrating an electro-acoustic hearing prosthesis and an intra-operative system for use during implantation of the electro-acoustic hearing prosthesis in accordance with embodiments presented herein.

Auditory/hearing prosthesis recipients suffer from different types of hearing loss (e.g., conductive and/or sensorineural) and/or different degrees/severity of hearing loss. However, it is now common for many hearing prosthesis recipients to retain some residual acoustic hearing ability (residual hearing). An electro-acoustic hearing prosthesis is a type of implantable hearing prosthesis that capitalizes on a recipient's residual hearing by delivering both acoustic stimulation (i.e., acoustic stimulation signals) and electrical stimulation (i.e., electrical stimulation signals), possibly simultaneously, to the same ear of a recipient. Typically, due to the limits of residual hearing in the implanted ear, the acoustic stimulation is used to present sound signal components corresponding to the lower frequencies of input sound signals (as determined from the residual hearing capabilities of the implanted ear), while the electrical stimulation is used to present sound signal components corresponding to the higher frequencies. The tonotopic region of the cochlea where the sound or stimulation output transitions from acoustic stimulation to electric stimulation is called the cross-over frequency region.

Recipients of electro-acoustic hearing prostheses typically benefit from having the acoustic stimulation in addition to the electrical stimulation, as the acoustic stimulation adds a more "natural" sound to their hearing perception relative to delivery of only electrical stimulation signals. The addition of the acoustic stimulation can, in some cases, also provide improved pitch and music perception and/or appreciation, as the acoustic signals may contain a more salient lower frequency (e.g., fundamental pitch, F0) representation than is possible with electrical stimulation. Other benefits of electro-acoustic hearing prosthesis may include, for example, improved sound localization, binaural release from unmasking, an increased ability to distinguish sounds in a noisy environment, etc.

Due to the benefits of combined acoustic-electric hearing, there is a desire to preserve as much of the recipient's residual hearing as possible during implantation of the stimulating assembly into a recipient's cochlea. Progressive improvements in the design of intra-cochlear stimulating assemblies (electrode arrays), surgical implantation techniques, tooling, etc. have enabled atraumatic surgeries which preserve at least some of the recipient's fine inner ear structures (e.g., cochlea hair cells) and the natural cochlea function, particularly in the higher frequency regions of the cochlea. With these improvements, clinical outcomes for recipients have improved significantly. Nonetheless, many factors may compound the probability of a good surgical outcome, including surgical skill and experience of the surgeon(s), cochlear anatomy, stimulating assembly type, etc. As a result, there remain cases in which the stimulating assembly insertion and associated surgical practices result in significant trauma to the cochlea and/or improper placement, thereby reducing the recipient's residual hearing and resulting in suboptimal clinical benefit.

Presented herein are techniques for objectively monitoring the insertion of an intra-cochlear stimulating assembly for the occurrence of one or more "insertion stop conditions." The insertion stop conditions are objectively detectable events indicating that insertion of the stimulating assembly into a recipient's cochlea should be at least temporarily stopped/ceased. The insertion monitoring is based on objectively measured inner ear responses/potentials, such as acoustically-evoked potentials. More specifically, in one form, the measured inner ear potentials are used to determine when a stimulating assembly has been inserted to a pre-selected/programmed insertion depth that is derived from one or more pre-operative measurements, such as an audiogram. In another form, the measured inner ear potentials are used to determine if the stimulating assembly contacts an internal structure of the cochlea, such as the basilar membrane, during the insertion procedure (e.g., at the distal end of the stimulating assembly or along the length of the stimulating assembly).

As described further below, a pre-selected insertion depth for a stimulating assembly, which is defined in terms of a frequency corresponding to residual hearing of the recipient, is referred to herein as a "target stop point." In other words, a target stop point is a pre-operatively defined insertion stop frequency. A "target stop condition" occurs when the stimulating assembly is inserted into the cochlea such that a portion of the stimulating assembly (e.g., a distal end of the stimulating assembly and/or one or more stimulating contacts) is located at a tonotopic region corresponding to the pre-operatively defined insertion stop frequency. Contact with an internal structure of the cochlea that is likely to impeded residual hearing, such as impingement on the basilar membrane, is referred to herein as an "error stop point" so as to trigger an "error stop condition."

In accordance with the techniques presented herein, detection of one of these two types of "stop points" or "stop conditions" triggers a feedback mechanism to stop or alter the insertion process. For example, the feedback mechanism may operate to halt automated insertion of a stimulating assembly (e.g., in a robotic or automated insertion) and/or to generate a notification to a surgeon (e.g., a notification to halt insertion of the stimulating assembly). In general, the error stop condition operates as a safety mechanism that is able to detect adverse events that occur during the insertion process, while the target stop condition provides the surgeon with evidence-based information that is recipient-centric (personalized) and standardized across recipient populations.

Also as described below, in addition to the stop conditions, embodiments of the present invention can also detect one or more "insertion warning conditions." An insertion warning condition occurs when the system determines that insertion of the stimulating assembly is approaching, or is likely to soon satisfy, one of the insertion stop conditions. The detection of an insertion warning condition may result in the initiation of a feedback mechanism indicating that insertion of the stimulating assembly into the cochlea should be slowed (e.g., to slow automated forward movement of a stimulating assembly, an alert or notification to a surgeon to slow forward movement, modify insertion to prevent motion of the stimulating assembly outwards towards the scala wall, etc.).

For ease of illustration, embodiments are primarily described herein with reference to insertion of stimulating assemblies forming part of an electro-acoustic hearing prosthesis comprising a cochlear implant portion and a hearing aid portion. However, it is to be appreciated that the techniques presented herein may be used with other types of hearing prostheses systems, such as systems that include cochlear implants, auditory brainstem implants, bi-modal hearing prostheses, electro-acoustic hearing prostheses comprising other types of output devices (e.g., auditory brainstem stimulators portions, direct acoustic stimulator portions, bone conduction device portions, etc.), etc.

Figure 1B:
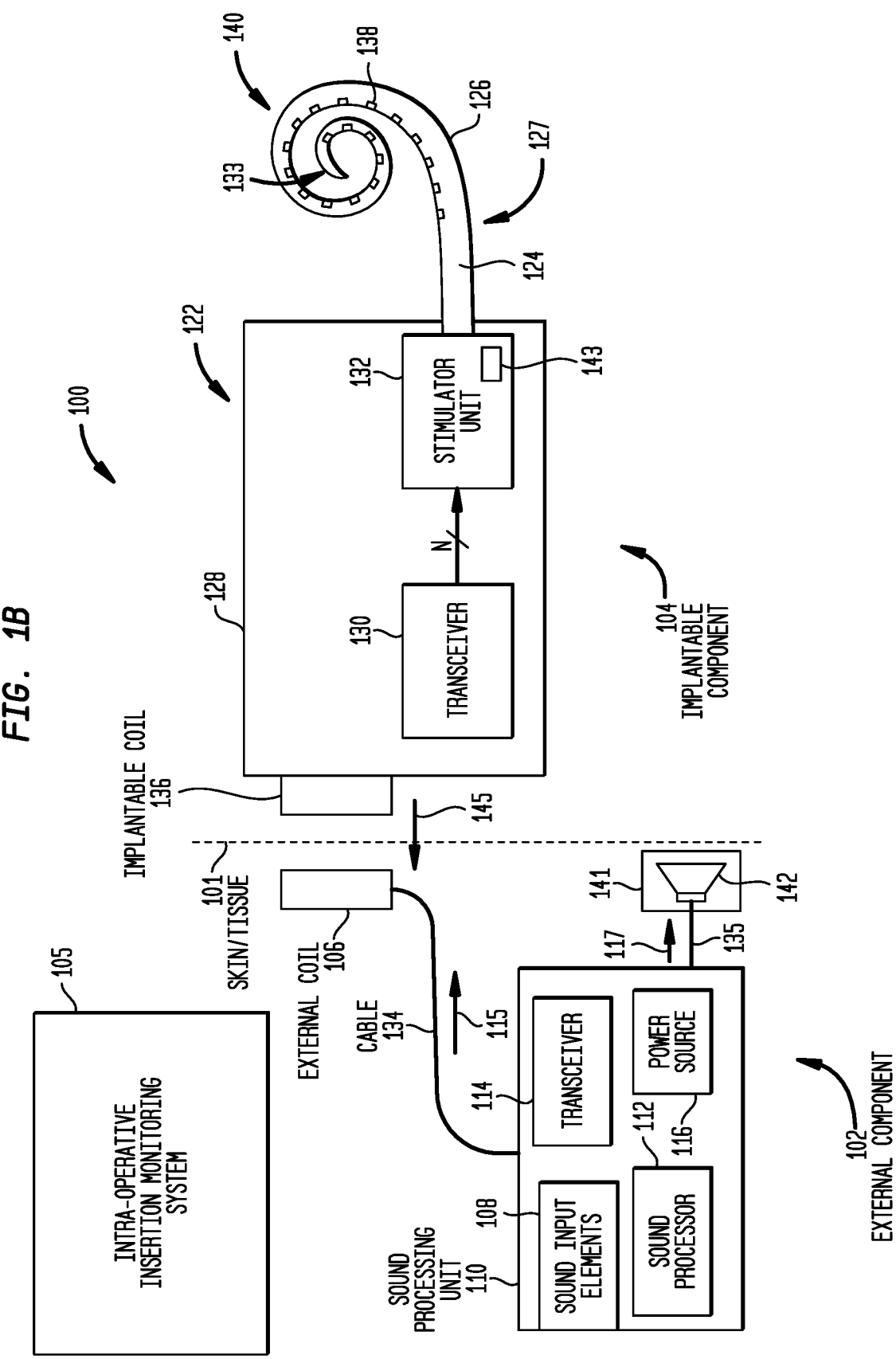
FIG. 1B is a block diagram illustrating further details of the electro-acoustic hearing prosthesis shown in FIG. 1A.

FIGS. 1A and 1B are diagrams of an illustrative intra-operative insertion monitoring system (intra-operative system) 105 configured to implement the techniques presented herein during implantation of implantable hearing prosthesis. To facilitate understanding of the techniques presented herein, the intra-operative system 105 is shown with an example electro-acoustic hearing prosthesis 100.

The illustrative intra-operative system 105 can be, for example, a computing device, such as a remote assistant for the hearing prosthesis, a computer (e.g., laptop, desktop, tablet), mobile phone, etc., or other device configured for communication with the electro-acoustic hearing prosthesis 100, In certain embodiments, the intra-operative system 105 may include both a computing device and an external component of a hearing prosthesis. Before describing details of the intra-operative system 105 and the insertion monitoring techniques presented herein, a description of the implantable electro-acoustic hearing prosthesis 100 is first provided below for context. As shown in FIGS. 1A and 1B, the electro-acoustic hearing prosthesis 100 includes an external component 102 and an internal/implantable component 104. The external component 102 is configured to be directly or indirectly attached to the body of a recipient, while the implantable component 104 is configured to be subcutaneously implanted within the recipient (i.e., under the skin/tissue of the recipient).

The external component 102 comprises a sound processing unit 110, an external coil 106, and, generally, a magnet (not shown in FIG. 1A) fixed relative to the external coil 106. The external coil 106 is connected to the sound processing unit 110 via a cable 134. The sound processing unit 110 comprises one or more sound input elements 108 (e.g., microphones, audio input ports, cable ports, telecoils, a wireless transceiver, etc.), a wireless transceiver 114, a sound processor 112, and a power source 116. The sound processing unit 110 may be, for example, a behind-the-ear (BTE) sound processing unit, a body-worn sound processing unit, a button sound processing unit, etc.

Connected to the sound processing unit 110 (e.g., via a cable 135) is a hearing aid component 141. The hearing aid component 141 includes a receiver 142 (FIG. 1B) that may be, for example, positioned in or near the recipient's outer ear. The receiver 142 is an acoustic transducer that is configured to deliver acoustic signals (acoustic stimulation signals) to the recipient via the recipient's ear canal and middle ear.

As shown in FIG. 1B, the implantable component 104 comprises an implant body (main module) 122, a lead region 124, and an elongate intra-cochlear stimulating assembly 126. The implant body 122 generally comprises a hermetically-sealed housing 128 in which an internal transceiver unit (transceiver) 130 and a stimulator unit 132 are disposed. The implant body 122 also includes an internal/implantable coil 136 that is generally external to the housing 128, but which is connected to the transceiver 130 via a hermetic feedthrough (not shown in FIG. 1B). Implantable coil 136 is typically a wire antenna coil comprised of multiple turns of electrically insulated single-strand or multi-strand platinum or gold wire. The electrical insulation of implantable coil 136 is provided by a flexible molding (e.g., silicone molding), which is not shown in FIG. 1B. Generally, a magnet is fixed relative to the implantable coil 136.

Elongate stimulating assembly 126 is configured to be at least partially implanted in the recipient's cochlea 120 (FIG. 1A) and includes a plurality of longitudinally spaced intra-cochlear electrical stimulating contacts (electrodes) 138 that collectively form a contact array 140 for delivery of electrical stimulation (current) to the recipient's cochlea. Stimulating assembly 126, which has a distal end 133 and a proximal end 127, extends through an opening 121 in the cochlea (e.g., cochleostomy, the round window, etc.). The proximal end 127 is connected to stimulator unit 132 via lead region 124 and a hermetic feedthrough (not shown in FIG. 1B). Lead region 124 includes a plurality of conductors (wires) that electrically couple the electrodes 138 to the stimulator unit 132.

Returning to external component 102, the sound input element(s) 108 are configured to detect/receive input sound signals and to generate electrical input signals therefrom. The sound processor 112 is configured execute sound processing and coding to convert the electrical input signals received from the sound input elements into output signals that represent acoustic and/or electric (current) stimulation for delivery to the recipient. That is, as noted, the electro-acoustic hearing prosthesis 100 operates to evoke perception by the recipient of sound signals received by the sound input elements 108 through the delivery of one or both of electrical stimulation signals and acoustic stimulation signals to the recipient. As such, depending on a variety of factors, the sound processor 112 is configured to convert the electrical input signals received from the sound input elements into a first set of output signals representative of electrical stimulation and/or into a second set of output signals representative of acoustic stimulation. The output signals representative of electrical stimulation are represented in FIG. 1B by arrow 115, while the output signals representative of acoustic stimulation are represented in FIG. 1B by arrow 117.

The output signals 115 are, in the examples of FIGS. 1A and 1B, encoded data signals that are sent to the implantable component 104 via external coil 106. More specifically, the magnets fixed relative to the external coil 106 and the implantable coil 136 facilitate the operational alignment of the external coil 106 with the implantable coil 136. This operational alignment of the coils enables the external coil 106 to transmit the encoded data signals, as well as power signals received from power source 116, to the implantable coil 136. In certain examples, external coil 106 transmits the signals to implantable coil 136 via a radio frequency (RF) link. However, various other types of energy transfer, such as infrared (IR), electromagnetic, capacitive and inductive transfer, may be used to transfer the power and/or data from an external component to an electro-acoustic hearing prosthesis and, as such, FIG. 1B illustrates only one example arrangement.

In general, the encoded data and power signals are received at the transceiver 130 and are provided to the stimulator unit 132. The stimulator unit 132 is configured to utilize the encoded data signals to generate electrical stimulation signals (e.g., current signals) for delivery to the recipient's cochlea via one or more stimulating contacts 138 this way, electro-acoustic hearing prosthesis 100 electrically stimulates the recipient's auditory nerve cells, bypassing absent or defective hair cells that normally transduce acoustic vibrations into neural activity, in a manner that causes the recipient to perceive one or more components of the received sound signals.

As noted above, it is common for hearing prosthesis recipients to retain at least part of this normal hearing functionality (i.e., retain at least one residual hearing). Therefore, the cochlea of a hearing prosthesis recipient can be acoustically stimulated upon delivery of a sound signal to the recipient's outer ear. In the example of FIGS. 1A and 1B, the receiver 142 is used to provide the acoustic stimulation. That is, the receiver 142 is configured to utilize the output signals 117 to generate acoustic stimulation signals that are provided to the recipient's cochlea via the middle ear bones and oval window, thereby creating waves of fluid motion of the perilymph within the cochlea.

Although FIGS. 1A and 1B illustrate the use of a receiver 142 to deliver acoustic stimulation to the recipient, it is to be appreciated that other types of devices may be used in other embodiments. It is also to be appreciated that embodiments of the present invention may be implemented in other hearing prostheses and other arrangements that shown in FIGS. 1A and 1B. For example, it is to be appreciated that embodiments of the present invention may be implemented with fully-implantable hearing prostheses in which the sound processor, power supply, etc. are all implanted within a recipient so that the hearing prosthesis may operate, for at least a period of time, without the presence of an external component. It is also to be appreciated that the embodiments of the present invention may be implemented with implantable hearing prostheses that do not deliver acoustic stimulation to a recipient (e.g., cochlear implants, auditory brainstem stimulators, etc.).

As noted, elongate stimulating assembly 126 is configured to be at least partially implanted in the recipient's cochlea 120. During implantation of the elongate stimulating assembly 126, it is important that the insertion is atraumatic to cochlear structures and residual hearing (i.e., does not damage the delicate structures of the inner ear), and positioned appropriately (e.g., proper depth to provide adequate electrical hearing given the type of hearing loss and does not interfere with the biophysical mechanisms associated with acoustic hearing) for clinical benefit.

Presented herein are techniques that use real-time objective metrics in the form of measured inner ear potentials, such as acoustically-evoked responses, to achieve these and other benefits. In particular, the intra-operative system 105 is configured to receive measured inner ear potentials from the electro-acoustic hearing prosthesis 100 during insertion of the stimulating assembly 126 into the recipient's cochlea. The measured inner ear potentials are obtained by delivering known electrical and/or acoustic stimulation to the recipient's auditory system, and recording the resulting potentials via one or more stimulating contacts 138 and one or more amplifiers 143 (FIG. 1B) located in the implantable component 104 (i.e., integrated amplifier of the cochlear implant captures one or more windows of the evoked activity). The measured inner ear potentials, which are generally represented in FIG. 1B by arrow 145, are transmitted back to the external component 102 for relay to the intra-operative system 105 or are transmitted directly to the intra-operative system 105. Using the measured inner ear potentials, the intra-operative system 105 is configured to determine whether insertion of stimulating assembly has encountered an insertion stop condition, such as a target stop condition or an error stop condition, or an insertion warning condition. Detection of one of a stop or warning condition causes the intra-operative system 105 to initiate a feedback mechanism to effect at least a temporary cessation of the insertion process.

As used herein, "inner ear potentials" refer to any voltage potential associated with either the electrical properties of the inner ear or its physiological function and/or potentials obtained via measurements at the inner ear. Potentials of a physiological nature (i.e., potentials relating to the physiological function of the inner ear), include acoustically-evoked potentials/responses (e.g., electrocochleography (ECoG) responses) and electrically-evoked potentials/response (e.g., electrically evoked compound action potential (ECAP) responses. Other potentials of a physiological nature are referred to herein as higher evoked potentials, which are potentials related to the brainstem and auditory cortex, inclusive of the electrical auditory brainstem responses (EABR), the middle latency response, and cortical responses. Potentials of a physiological nature are sometimes referred to herein as "physiological potentials." Potentials of electrical nature (i.e., potentials relating to the electrical properties of the inner ear itself or intra-cochlear contacts) include voltage tomography responses, measured impedances (bulk and interface), and/or other forms of electrode (stimulating contact) voltage measurements. Potentials of electrical nature are sometimes referred to herein as "physiological electrical potentials."

As used herein, an ECoG measurement refers to the capture of a set of potentials generated in a recipient's cochlea in response to the delivery of acoustic stimulation to the cochlea. A captured set of potentials (i.e., an ECoG response) may include a plurality of different stimulus related potentials, such as the cochlear microphonic (CM), the cochlear summating potential (SP), the auditory nerve neurophonic (ANN), and the auditory nerve or Compound Action Potential (CAP), which are measured independently or in various combinations. The potentials captured as part of an ECoG response are a form of acoustically-evoked cochlear responses.

The cochlear microphonic is a fluctuating voltage that mirrors the waveform of the acoustic stimulus at low, moderate, and high levels of acoustic stimulation. The cochlear microphonic is generated by the outer hair cells of the organ of Corti and is dependent on the proximity of the recording electrode(s) to the stimulated hair cells and the basilar membrane. In general, the cochlear microphonic is proportional to the displacement of the basilar membrane by the travelling wave phenomena.

The summating potential is the direct current (DC) response of the outer hair cells of the organ of Corti as they move in conjunction with the basilar membrane (i.e., reflects the time-displacement pattern of the cochlear partition in response to the stimulus envelope). The summating potential is the stimulus-related potential of the cochlea and can be seen as a DC (unidirectional) shift in the cochlear microphonic baseline. The direction of this shift (i.e., positive or negative) is dependent on a complex interaction between stimulus parameters and the location of the recording electrode(s).

The auditory nerve neurophonic is a signal recorded from the auditory nerve, while the auditory nerve Action Potential represents the summed response of the synchronous firing of the nerve fibers in response to the acoustic stimuli, and it appears as a fluctuating voltage. The auditory nerve Action Potential is characterized by a series of brief, predominantly negative peaks, including a first negative peak (N1) and second negative peak (N2). The auditory nerve Action Potential also includes a magnitude and a latency. The magnitude of the auditory nerve Action Potential reflects the number of fibers that are firing, while the latency of the auditory nerve Action Potential is measured as the time between the onset and the first negative peak (N1).

As noted above, the techniques presented herein are configured to monitor the insertion of a stimulating assembly for detection of a warning or stop condition (e.g., target stop condition and/or an error stop condition). FIG. 2A is a schematic diagram schematically illustrating the concept of a pre-operatively defined insertion stop frequency (target stop point) that corresponds to a target stop condition in accordance with embodiments presented herein.

More specifically, a recipient's cochlea 120 is a conical spiral structure comprising three parallel fluid-filled canals or ducts, collectively and generally referred to herein as canals. For ease of illustration, FIG. 2A illustrates cochlea 120 in an "unrolled" arrangement. The cochlea canals comprise the tympanic canal 146, also referred to as the scala tympani, the vestibular canal 148, also referred to as the scala vestibuli, and the median canal 150, also referred to as the scala media. Cochlea 140 spirals about a recipient's modiolus (not shown) several times and terminates at cochlea apex 152.

Separating the cochlea canals are various membranes and other tissue. In particular, toward a lateral side of the scala tympani 146, a basilar membrane 154 separates the scala tympani 146 from the scala media 150. Similarly, toward lateral side of the scala vestibuli 148, a vestibular membrane 156, also referred to as the Reissner's membrane, separates the scala vestibuli 148 from the scala media 150.

The scala tympani 146 and the scala vestibuli 148 are filled with a fluid, referred to herein as perilymph, which has different properties than that of the fluid which fills the scala media 148, referred to as endolymph, and which surrounds the organ of Corti (not shown). Sound entering the auricle of a recipient's ear causes pressure changes in cochlea 120 to travel through the fluid-filled tympanic and vestibular canals 146, 148. The organ of Corti, which is situated on basilar membrane 154 in scala typmani 146, contains rows of 16,000-20,000 hair cells (not shown) which protrude from its surface. Above them is the tectoral membrane which moves in response to pressure variations in the fluid-filled tympanic and vestibular canals 146, 148. Small relative movements of the layers of the tectoral membrane are sufficient to cause the hair cells in the endolymph to move thereby causing the creation of a voltage pulse or action potential which travels along the associated nerve fiber to the auditory areas of the brain for processing.

The place along basilar membrane 154 where maximum excitation of the hair cells occurs determines the perception of pitch and loudness according to the place theory. Due to this anatomical arrangement, cochlea 120 has characteristically been referred to as being "tonotopically mapped." That is, regions of cochlea 120 toward basal region 160 are responsive to higher frequency signals, while regions of cochlea 120 toward apical region 162 are responsive to lower frequency signals. For example, the proximal end of the basal region 160 is generally responsible to 20 kilohertz (kHz) sounds, while the distal end of the apical region is responsive to sounds at around 200 hertz (Hz).

In hearing prosthesis recipients, residual hearing most often is present within the lower frequency ranges (i.e., the more apical regions of the cochlea) and little or no residual hearing is present in the higher frequency ranges (i.e., the more basal regions of the cochlea). This property of residual hearing is exploited in electro-acoustic hearing prostheses where the stimulating assembly is inserted into the basal region and is used to deliver electrical stimulation signals to evoke perception of higher frequency sounds. Ideally, insertion of the stimulating assembly is terminated before reaching the functioning regions of the cochlea where there is residual hearing so that remaining hair cells are able to naturally perceive lower frequency sounds that cause movement of the perilymph. This concept is illustrated in FIG. 2A where reference 164 illustrates the region of the cochlea 120 to which electrical stimulation is delivered to evoke hearing perception, while reference 166 illustrates the region of the cochlea 120 that utilizes acoustic stimulation to evoke a hearing perception.

The tonotopic region of the cochlea 120 where the sound or stimulation output transitions from the acoustic stimulation to the electric stimulation is called the cross-over frequency region, and is illustrated in FIG. 2A by reference 168. Recipient's of electro-acoustic hearing prosthesis may have different residual hearing characteristics and, accordingly, different cross-over frequency regions (i.e., transitions occur at different tonotopic regions of the cochlea). Additionally, insertion of the distal end of a stimulating assembly into and/or past the cross-over frequency region can interfere with, or damage, the recipient's residual hearing. Therefore, as noted above, an objective of the techniques presented herein is to provide a surgeon with objective measurements that enable insertion of a stimulating assembly to be halted at a depth, referred to elsewhere herein as the target stop point, that does not interfere with or damage the recipient's residual hearing. The target stop point, which is defined as a specific frequency or a specific frequency range (pre-operatively defined insertion stop frequency), is represented in FIG. 2A by reference 170. Also as noted elsewhere herein, a target stop condition occurs when the distal end or other portion of a stimulating assembly is inserted to a location (depth) within the cochlea that corresponds to (i.e., at or near) the pre-operatively defined insertion stop frequency (i.e., the specific frequency or a specific frequency range of the target stop point).

As noted above, the intra-operative system 105 may utilize any of a number of different types of inner ear potential measurements to determine when the stimulating assembly 126 has encountered an insertion stop or warning condition. FIG. 2B is a graph 169 illustrating how inner ear responses in the form of cochlear microphonic amplitudes can be used to determine when a measurement contact approaches, reaches, and passes a tonotopic region of the cochlea associated with a target stop point. The graph 169 of FIG. 2B has a vertical axis that represents the amplitude of a measured cochlear microphonic amplitudes and a horizontal axis that represents time.

In the example of FIG. 2B, the cochlea 120 of the recipient is stimulated with an acoustic input having at least one selected frequency that is associated with (i.e., corresponds to) a specific tonotopic region of the cochlea 120. As the stimulating assembly 126 is inserted into the cochlea 120, at least one contact of the stimulating assembly 126 (i.e., the measurement contact) is used to obtain ECoG measurements, which include the cochlear microphonic amplitude. As shown by reference 171 in FIG. 2B, the amplitude of the cochlear microphonic gradually increases as the measurement contact approaches the tonotopic region of the cochlea associated with the frequency of the acoustic input. As shown by reference 173, the amplitude of the cochlear microphonic peaks when the measurement contact is located at the tonotopic region of the cochlea associated with the frequency of the acoustic input. Finally, as shown by reference 175, the amplitude of the cochlear microphonic gradually decreases as the measurement contact moves away from the tonotopic region of the cochlea associated with the frequency of the acoustic input.

As noted above, an objective of the insertion process is to stop insertion of the stimulating assembly 126 when a portion of the stimulating assembly (e.g., a distal end of the stimulating assembly and/or one or more stimulating contacts) reaches, but does not pass, a tonotopic region corresponding to the pre-operatively defined insertion stop frequency (i.e., the target stop point). Therefore, FIG. 2B is merely illustrative and does not represent cochlear microphonic amplitudes that would be measured in all embodiments. Instead, when the cochlear microphonic amplitude is measured at the pre-operatively defined insertion stop frequency, the insertion could stop at points 171 or, ideally, 173 of FIG. 2B (i.e., before the measurement contact passes the target stop point).

In addition to a target stop condition, embodiments presented herein are also configured to monitor insertion of a stimulating assembly for warning conditions or an error stop condition. An error stop condition occurs when a stimulating assembly physically contacts or otherwise interferes with the organ of corti (including the basilar membrane 154) at any point along the stimulating assembly. Contact or interference may be due to, for example, over insertion, cochlea morphology, improper surgical trajectory, etc. Further details for detection of target stop conditions, an error stop conditions, and warning conditions are provided below.

Figure 3:
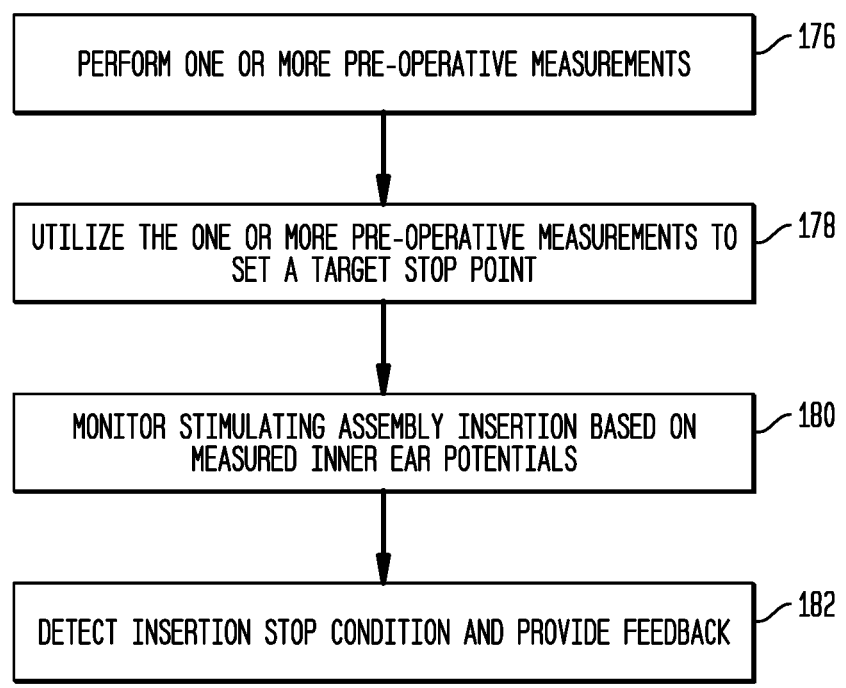
FIG. 3 is a flowchart of an example method in accordance with embodiments presented herein.

FIG. 3 is a flowchart illustrating operations associated with detection of one or more stop conditions in accordance with embodiments presented herein. For ease of illustration, the method of FIG. 3 is described with reference to the intra-operative system 105 and the electro-acoustic hearing prosthesis 100 of FIGS. 1A and 1B.

The method 175 of FIG. 3 begins at 176 where one or more pre-operative tests/measurements are performed on the recipient to assess the function of cochlea 120 (i.e., the cochlea in which the stimulating assembly 126 is to be implanted). The one or more pre-operative tests can include an audiogram measurement of the recipient's cochlea 120 in order to record the recipient's residual hearing (i.e., to determine the frequency and/frequency range where the recipient's residual hearing begins). An audiogram measurement refers to a behavioral hearing test, sometimes referred to as audiometry, which generates an audiogram. The behavioral test involves the delivery of different tones, presented at a specific frequency (pitch) and intensity (loudness), to the recipient's cochlea and the recording of the recipient's subjective responses. The resulting audiogram is a graph that illustrates the audible threshold for standardized frequencies as measured by an audiometer. In general, audiograms are set out with frequency in Hertz (Hz) on the horizontal (X) axis, most commonly on a logarithmic scale, and a linear decibels Hearing Level (dBHL) scale on the vertical (Y) axis. In certain arrangements, the recipient's threshold of hearing is plotted relative to a standardized curve that represents 'normal' hearing, in dBHL. The audiogram is used to determine the frequency and threshold of hearing for the recipient's cochlea.

In addition to an audiogram measurement, the pre-operative tests can also include one or more imaging tests, such as a high resolution computed tomography (CT) scan, X-ray, Magnetic resonance imaging (MRI), etc. of the recipient's cochlea. In certain embodiments, the high resolution CT scan, and possibly the MRI, is employed clinically to determine if there are anatomical abnormalities or bone growth (meningitis) prior to the surgery. The MRI can also be used to determine the viability of the auditory nerve. Moreover, the size of the cochlea may be assessed (estimated) via high resolution CT scans that measure the anatomical landmarks, which can be used to assist with the prediction of insertion depth angles.

The one or more pre-operative tests can also include an initial inner potential measurement, such as an ECoG measurement, that is performed from outside of the cochlea (e.g., the round window). The inner potential measurements can be taken pre-operatively, using a measurement electrode that is inserted through the tympanic membrane, or intra-operatively before beginning insertion of the stimulating assembly 126 (i.e., before drilling the cochleostomy or making the incision in the round window). In the case of an ECoG measurement, ECoG responses are evoked using an acoustic input at a number of different frequencies and a fixed presentation level (e.g., supra-threshold). As such, a pre-operative ECoG measurement provides a baseline recording of the ECoG responses at each of a number of different frequencies along the length of the cochlea 120, along with the relative magnitude information between each frequency to indicate a region where maximum ECoG amplitude can be expected for each frequency.

At 178, the results of the pre-operative measurements (e.g., audiogram, CT scan, initial inner potential measurement, etc.) are used to set a target stop point for the stimulating assembly 126. As noted above, a target stop point is a cochlea frequency or frequency range, sometimes referred to herein as a pre-operatively defined insertion stop frequency, to which a distal end 133 of the stimulating assembly 126 is expected to be inserted so as to be located at or near the tonotopic region where the recipient's residual hearing begins. In certain embodiments, the target stop point is set at a conservative frequency or frequency range that would minimize the probability of causing either unrecoverable or permanent damage to the residual hearing. As such, the target stop depth is a type of predictive estimate or target that, as described below, is monitored and possibly refined during the insertion process.

In certain embodiments, normative statistics generated based on prior implantations for similar recipients can be used to further refine the target stop point (i.e., revise the target stop depth based on information determined from other recipients having similar characteristics/attributes to the subject recipient). For example, the refinement based on normative statistics can be made by taking into account the recipient's age (i.e., refine based on implantation results from similarly aged recipients), the one or more imaging tests (e.g., based on implantation results for recipient's having similar X-rays, CT scans, etc.), hearing loss, aetiology or other shared characteristics.

In addition to the target stop point, the results of the pre-operative measurements can also be used to set a minimum insertion depth. The minimum insertion depth defines the depth to which the distal end 133 of the stimulating assembly 126 is estimated to be implanted in the cochlea in order to provide acceptable electrical only hearing performance (e.g., based on existing clinical evidence). This minimum insertion depth would take into account anatomical differences (e.g., smaller cochlea sizes, malformations, etc.) identified by the pre-operative measurements. In general, the minimum insertion depth could be specified as a frequency, frequency range, or an angle. Defining the minimum insertion depth as an angle takes into account the variations in the cochlea anatomical size and the electrode type (modiolar or lateral wall), etc.

In general, it has been determined that for electrical-only hearing (i.e., only electrical stimulation) with a full length array, there is a minimum insertion depth where maximum clinical benefit can be obtained. Any insertion depth that is under this is distance, again for electrical-only hearing, will have a poor clinical outcome. It is also expected that, for some recipients, residual acoustic hearing will eventually reduce, leaving only the electrical hearing abilities. For recipient's likely willing to undergo revision surgery (e.g., children), the minimum insertion depth may be an insertion depth where it is ensured that the acoustic hearing is fully unperterbed by the introduction of the stimulating assembly. For recipient's unlikely to undergo an additional surgery (e.g., older recipients), the minimum insertion depth may be a depth where it is determined that, when the residual acoustic hearing deteriorates, the implanted stimulating assembly will still provide acceptable electrical-only performance.

After setting the target stop point and the minimum insertion depth, the surgeon begins implantation of the stimulating assembly (e.g. opens the cochleostomy or incises the round window and inserts the distal end into the cochlea). At 180, the insertion of the stimulating assembly 126 is monitored using objective inner ear potentials measured, in real-time, via one or more stimulating contacts 138. For example, in certain embodiments one or more acoustic tones (e.g., pure tone(s)) at a selected frequency or frequencies are delivered to the recipient's outer ear using, for example, the receiver 142. The acoustic signals delivered by the receiver 142 cause displacement waveforms that travel along the basilar membrane. These waves grow in amplitude and reach a maximum at the characteristics frequency (CF) as a function of frequency along the cochlea. These vibrations along the cochlea give rise to an inner ear potential. Therefore, in response to the delivered acoustic signals, one or more of the stimulating contacts 128 and the integrated amplifier(s) 143 of the cochlear implant capture one or more windows of the evoked activity (i.e., perform ECoG measurements) to generate inner ear response measurements (e.g., ECoG response measurements) that are provided to the intra-operative system 105. In other words, the intra-operative system 105 monitors the inner ear response at one or more of the stimulating contacts 138.

In certain examples, the acoustic signals delivered by the receiver 142 are selected based on the results of the one or more pre-operative tests. For example, the acoustic signals can have a frequency that is the same as, or close to, the frequency of the target stop point (e.g., at a frequency where the augmented hearing (electrical and acoustic) offers the maximal clinical benefit, around a predetermined cutoff frequency where acoustic hearing starts, etc.,) determined from the pre-operative audiogram.

At 182, an insertion stop condition is detected and, in response to the detection, a feedback mechanism is initiated/triggered. As noted above, an insertion stop condition can include a target stop condition, meaning that the intra-operative system 105 has determined that a selection portion of the stimulating assembly 126 (e.g., distal end 133, one or more contacts 138, etc.) has reached the tonotopic region corresponding to the frequency defining the target stop point. If the target stop condition is detected, insertion of the stimulating assembly 126 should be terminated to prevent damage to the recipient's residual hearing.

Also as noted above, an insertion stop condition can also be an error stop condition, meaning that the stimulating assembly 126 has interfered with (e.g., come into physical contact with) an intra-cochlea structure, such as the basilar membrane. For example, it is possible that the stimulating assembly can move outwards towards the scala wall, at points other than the apical region of the stimulating assemble (e.g., a modiolar hugging array, which is flexible, can reach a point in the insertion when it meets physical resistance and bows outwards to the scala wall, riding up the wall to eventually make physical contact with the basilar membrane). If an error stop condition is detected, corrective action should be initiated.

In accordance with the embodiments presented herein, the insertion stop or warning conditions can be detected in a number of different manners. More specifically, referring first to the detection of a target stop condition, one or more objective inner ear potential measurements, such as ECoG measurements, are continually performed in real-time while the stimulating assembly 126 is inserted into the cochlea 120 (i.e., as the stimulating assembly 126 is moved in an apical direction). The intra-operative system 105 analyzes the measured real-time inner ear potentials relative to one another to determine if a change in the measured response occurs. The change may be, for example, an expected change in the magnitude/amplitude, phase, shape of the response/waveform (morphology), frequency, or other aspects of the responses. For example, in one embodiment, an expected change indicative of a target stop condition comprises the detection of a peak or near peak in acoustically-evoked inner ear potentials (e.g., CM components of ECoG responses).

Again, in accordance with embodiments presented herein, the real-time inner ear potential measurements can be made in a number of different manners at one or more locations (e.g., simultaneously, sequentially, etc.) within the cochlea. In certain embodiments, inner ear potential measurements can be used to monitor or track the progression of the stimulating assembly 126 within the cochlea 120 using one or more complex acoustic inputs (sound signals) comprising multiple frequencies. In other words, inner ear potential measurements can be performed based on several different acoustic frequencies and/or at different contacts of the stimulating assembly (i.e., multi-frequency acoustic inputs and/or multi-electrode/contact recording). The complex acoustic inputs may comprise, for example, a frequency sweep signal, a series of sound chirps, etc.

More specifically, the intra-operative system 105 can be configured to perform inner ear potential measurements at any of a number of contacts (in response to the same or different acoustic input), and then perform a comparison relative to another and/or against previous time points (e.g., pattern matching, correlation, etc.). Signal features that can be compared at, for example, different time points (cross-time point comparison) include phase, amplitude, morphology, etc. Based on the comparisons, the intra-operative system 105 could determine, for example, current insertion depth, location relative to the predicted depth, basilar membrane contact, stimulating assembly deformation (e.g., bowing), tonotopic mapping in the cochlea, changes to the acoustic resonant properties of the cochlea, etc.

In summary, the inner ear potential measurements in accordance with embodiments presented herein may make use of multi-electrode recording, complex acoustic inputs, cross-time comparisons, and/or cross-electrode comparisons. These variations could, for example, enable the system to gauge the current tonotopic position of the measurement contact(s) (e.g., apical electrode) and/or to set a baseline that makes early stage detection of a "shift" in the cochlea microphonic (such as a change in resonant frequency) easier to detect.

In certain embodiments, one or more complex acoustic inputs (e.g., a frequency sweep signal or a series of sound chirps) are used to correlate the position of one or more contacts with a frequency response as the array advances within the cochlea. That is, the one or more complex acoustic inputs enable the intra-operative system 105 to detect the current tonotopic position of one or more contacts and, accordingly, the position of the stimulating assembly 126. In one such example, one or more complex acoustic inputs are delivered to the cochlea 120 to evoke responses along the cochlea at tonotopic locations preceding the target frequency (i.e., frequencies that are higher than the target stop point). Using these responses, the intra-operative system 105 can then determine when the measurement contacts (e.g., the apical contact) approaches, reaches, and passes the tonotopic region of the cochlea associated with each of the frequencies. As noted above, FIG. 2B illustrates an example of a cochlear microphonic amplitude measured as a measurement contact approaches, reaches, and passes the tonotopic region of the cochlea 120 that corresponds to the frequency of an acoustic input.

In one specific example, one or more complex acoustic inputs having specific frequency components of at least 2 kHz, 1.5 kHz, 1 kHz, and 500 Hz are presented to the cochlea 120. In this example, the target stop point is 500 Hz. As the stimulating assembly 126 is inserted into the cochlea 120, ECoG measurements are performed at the most apical contact to obtain cochlear microphonic amplitudes for each of the tonotopic regions corresponding to the frequencies in the one or more complex acoustic inputs (e.g., at least 2 kHz, 1.5 kHz, 1 kHz, and 500 Hz). During insertion towards the target 500 Hz, the apical contact will approach, reach, and pass the tonotopic regions associated with 2 kHz, 1.5 kHz, 1 kHz, thereby rendering cochlear microphonic amplitudes similar to that shown in FIG. 2B (i.e., a rise, peak, and fall) at each of the corresponding tonotopic regions. Using the cochlear microphonic amplitudes measured at one or more of the tonotopic regions preceding the target stop point, the intra-operative system 105 could, for example, refine the target stop point, determine a dynamic trigger indicating that the target stop point has been reached, track the location of the apical contact, etc. In one specific example, the frequency band of the acoustic input can be reduced to frequencies adjacent the target frequency as the insertion depth approaches the target depth to give the system greater resolution.

For example, the cochlear microphonic amplitude peaks at two sequential tonotopic regions of the cochlea 120 (e.g., the 2 kHz region and the 1.5 kHz region) could be detected and analyzed relative to one another for translation into a distance measurement. That is, the intra-operative system 105 could, using a scaling of the cochlea, determine that the movement between two of the higher frequencies equates to a certain distance. Through multiple data points and cochlear scale, the intra-operative system 105 can determine how far past the 1 kHz region the stimulating assembly 126 should be inserted so as to reach the 500 Hz region. Accordingly, using these measurements, the intra-operative system 105 could then trigger a notification when the apical contact reaches or gets close to the 500 Hz region. In summary, the intra-operative system 105 could use the responses measured at earlier (higher) frequencies to determine and measure cochlea distances and, accordingly, improve the insertion process.

In another example, cochlear microphonic amplitude peaks detected at earlier sequential tonotopic regions of the cochlea 120 (e.g., the 2 kHz, 1.5 kHz, and 1 kHz regions) could be used to determine when the cochlear microphonic amplitude is approaching a peak, or has reached the peak, at the 500 Hz region. More specifically, the earlier cochlear microphonic amplitude peaks could be correlated with one another (e.g., pattern matching) to generate one or more recipient-specific "peak characteristics." As the apical contact approaches the 500 Hz, the intra-operative system 105 could analyze the measured cochlear microphonic for these recipient-specific peak characteristics and, accordingly, trigger a notification when the apical contact reaches or gets close to the 500 Hz region.

As noted above, embodiments presented herein may also make use of multi-electrode/contact recording. In one form, the multi-electrode recording enables the intra-operative system 105 to monitor patterns. For example, the intra-operative system 105 could record inner ear potential measurements for each frequency component at successive measurement contacts. If the acoustic input remains the same, the response recorded at each successive contact could be correlated with one other. In one example, deviations in the response profile across the cochlea could be indicate initial changes to the basilar membrane impedance.

The multi-electrode recording could also be used to gauge insertion depth from the neural response profile and, accordingly, prevent the stimulating assembly from passing the target stop point. In one example, each time a successive electrode contact passes an established neural response peak, the intra-operative system 105 can increment a cumulative insertion depth total by the distance between adjacent electrode contacts. Further to this, the insertion depth may be approximated by a pattern matching procedure whereby subsequent measurement contacts (non-apical) that pass by the earlier apical recording position are matched to provide a relative measure between measurement contacts. Given that the distance between contacts is known this, this distance may be then converted into an insertion depth measure.

In certain embodiments, the intra-operative system 105 begins to monitor the inner ear potentials for changes when the distal end 133 of the stimulating assembly 126 approaches the minimum insertion depth, where the forward movement of the stimulating assembly 126 is slowed. In other embodiments, the intra-operative system 105 begins to monitor the inner ear potentials for changes as soon as the one or more contacts used for measurement of the potentials enter the cochlea. Other starting points may be used in alternative embodiments.

In the event that a change in the measured inner ear potentials is detected, the intra-operative system 105 could trigger insertion of the stimulating assembly 126 to be halted for a period of time (e.g., stop automated insertion process, generate a notification to a surgeon, etc.). When the insertion is halted, the real-time inner ear potential measurements are continued and the intra-operative system 105 continues to monitor the measured potentials to determine if they return/recover to (i.e., to determine whether the identified change disappears). If no recovery is detected, then the intra-operative system 105, surgeon, etc. could initiate on or more remedial actions. For example, if it is determined that the distal end 133 of the stimulating assembly 126 has already passed the minimum insertion depth, then the intra-operative system 105 could determine that the target stop point has been reached (i.e., the target stop condition has occurred). As a result, insertion of the stimulating assembly 126 is ceased and the stimulating assembly is secured with the recipient. In other examples, a change in the measured inner ear potentials (e.g., a sharp drop in the cochlear microphonic) that doesn't recover is likely to indicate contact with the basilar membrane (i.e., an error stop) that could be addressed as described elsewhere herein.

As noted, the intra-operative system 105 is configured to monitor the measured inner ear potentials to determine if a change occurs (e.g., detects a change in the ECoG responses). In the event that no change is observed, the intra-operative system 105 compares the measured inner ear potentials at one or more acoustic frequencies against the pre-insertion inner ear potential response (e.g., the baseline). If, on comparison, the measured inner ear potentials approach the pre-insertion inner ear potential response, then insertion of the stimulating assembly 126 is halted. If the target stop point has been reached, then the stimulating assembly 126 is secured within the recipient.

In certain embodiments, when the stop point has been reached, the measured inner ear potentials would begin to decrease slightly (i.e., the measurement contact has begun to pass the excitory location). In the event the measurement contact has not reached the stop point, the signal is still increasing (i.e., still yet to reach the maximum value which is the stop point).

An error stop condition occurs when the intra-operative system 105 detects a significant change (e.g., magnitude reduction) in the measured inner ear potentials during the insertion before the target stop point has been reached. In this scenario, the insertion of the stimulating assembly 126 is halted for a period of time to determine if the measured inner ear potentials recover. If no recovery is detected, then corrective action is initiated.

For example, in one specific example, the stimulating assembly 126 can be partially retracted and the system monitors the cochlear to determine if the measured inner ear potentials recover. If no recovery is detected, then the intra-operative system 105, surgeon, etc. could initiate on or more remedial actions. For example, the stimulating assembly 126 could be further retracted and re-inserted using a new trajectory, the surgical plan could be revised to call for a full insertion, etc.

For example, a sharp drop in the magnitude (amplitude) of the cochlea microphonic (CM) in measured ECoG responses can indicate contact with the basilar membrane. More specifically, if the stimulating assembly physically contacts the basilar membrane, this contact changes the mechanical impedance of the basilar membrane which, in turn, reduces the magnitude of the CM (e.g., a physical impingement of the basilar membrane or partition will shift the resonant peak of the cochlea microphonic). This may be reversible by partially retracting the stimulating assembly to remove the mechanical impedance. However, contact with the basilar membrane can also, in certain circumstances, indicate a dynamic stop depth where greater insertion is likely to damage or further impede movement of the basilar membrane. It is also noted that the nature of the contact with the basilar membrane may be reliant on the stimulating assembly type in use. For example, a perimodiolar electrode may bow outwards at the back wall of the cochlea when nearing over insertion. As such, the techniques presented are configured to capture the inner ear potentials at different points along the array not just the apical contact. At any point along the insertion, if the intra-operative system 105 detects a shift in the cochlea microphonic, which can indicate contact with the internal structure of the cochlea (e.g., basilar membrane), then the system triggers an alert to stop the insertion. A premature stop (i.e., prior to the target stop point) can cause the surgeon to take some corrective action, such as retract the assembly, re-insert with a different trajectory, etc.

Figure 4A:
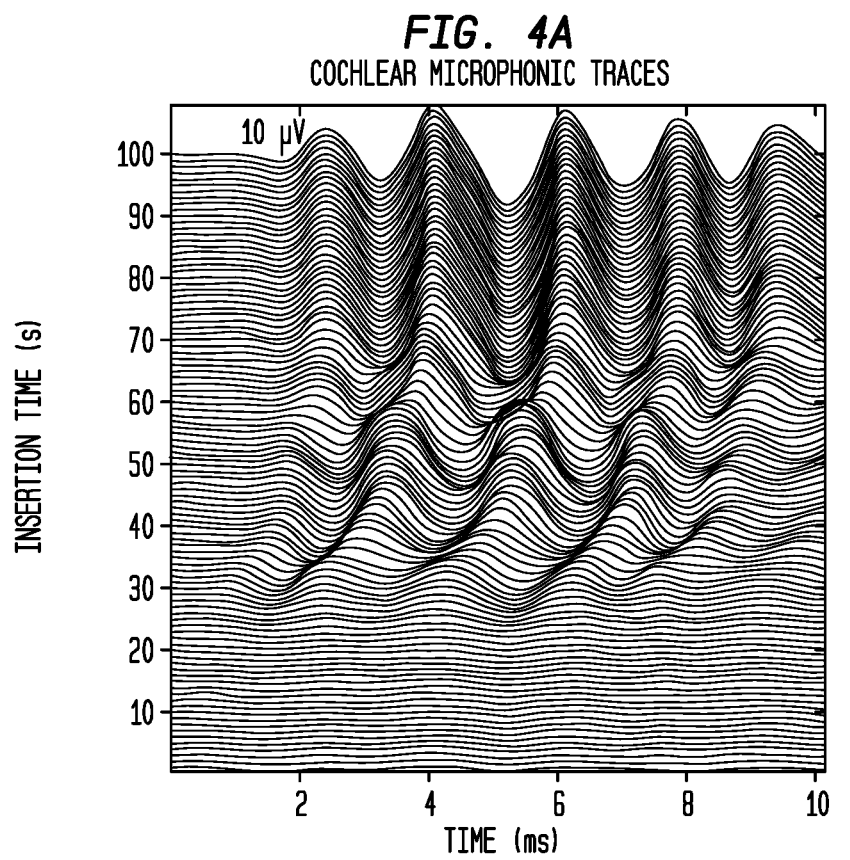
FIGS. 4A and 4B are diagrams illustrating cochlear microphonic amplitudes measured during an atraumatic insertion.
Figure 4B:
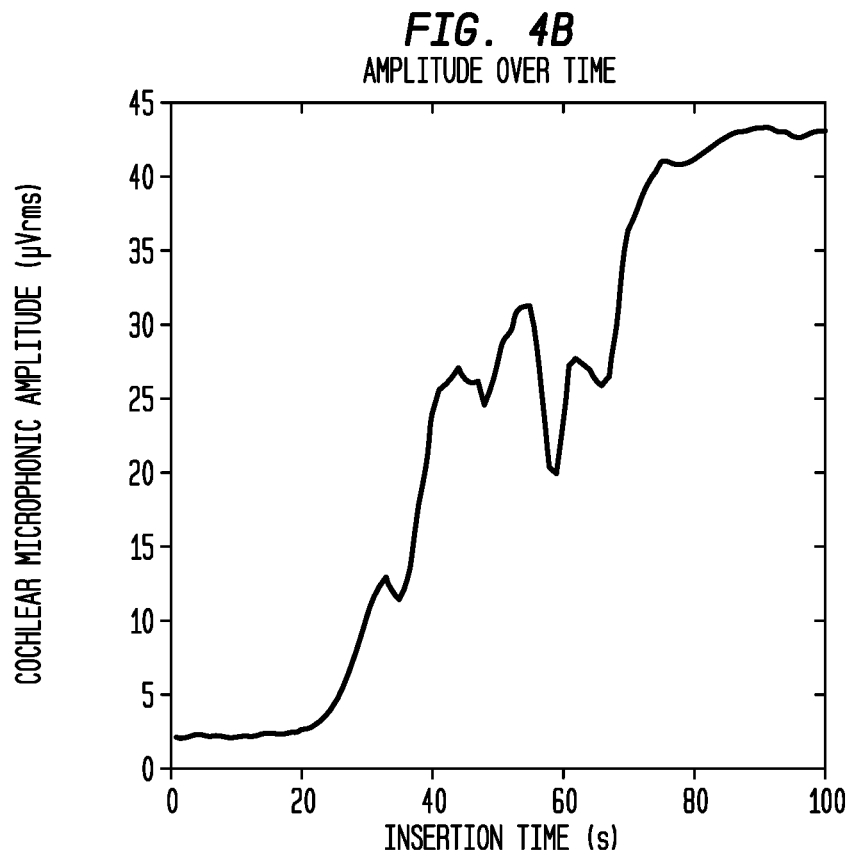
Figure 5A:
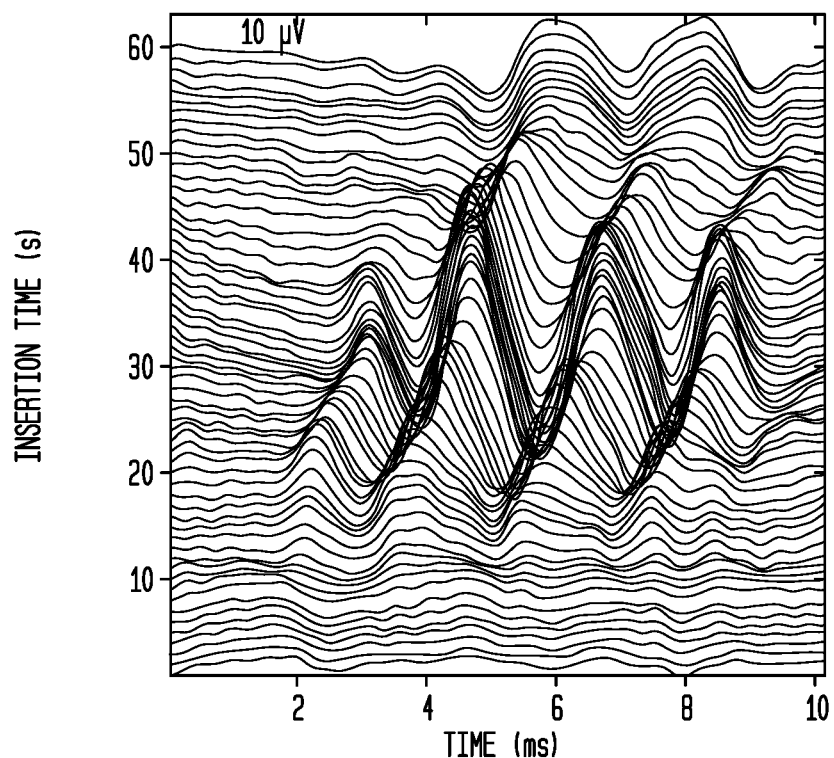
FIGS. 5A and 5B are diagrams illustrating cochlear microphonic amplitudes measured during a traumatic insertion.
Figure 5B:
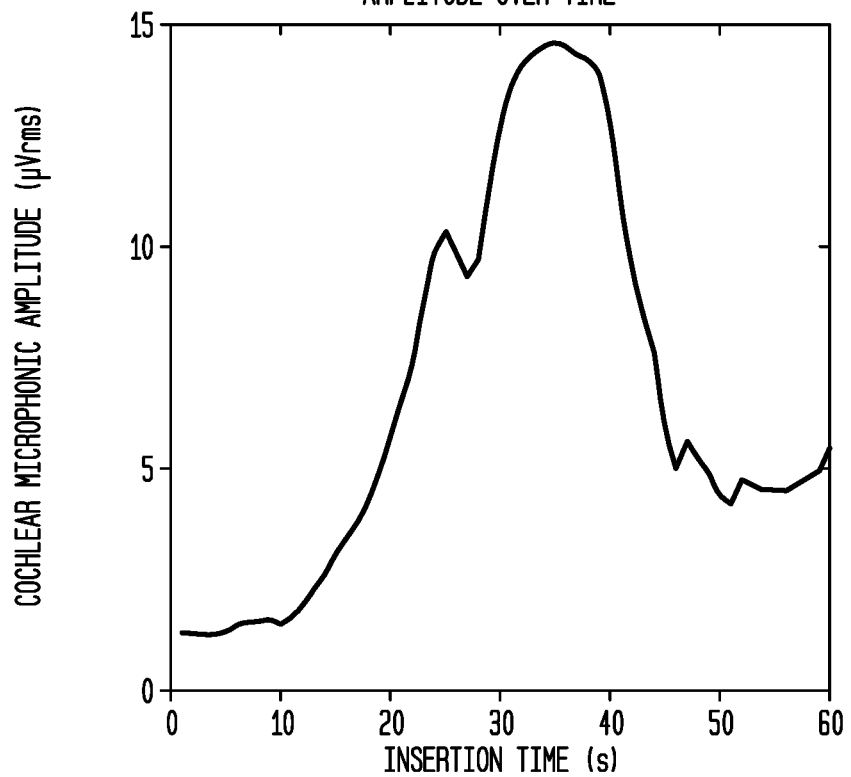

FIGS. 4A-4B and 5A-5B illustrate the detection of an error stop condition using the magnitude of the cochlea microphonic in a measured ECoG response. More specifically, FIGS. 4A-4B and 5A-5B illustrate cochlear microphonic traces at approximately 1 per second, when a stimulating assembly is inserted in two different recipients. FIGS. 4A and 4B illustrate an atraumatic insertion where the cochlear microphonic amplitude increases with insertion depth as the stimulating assembly approaches the target stop point. However, FIGS. 5A and 5B illustrate a more traumatic insertion where the cochlear microphonic amplitude initially increases with depth, but then significantly drops when the stimulating assembly contacts the basilar membrane.

As noted above, in addition to the stop conditions, embodiments of the present invention can also detect one or more insertion warning (i.e., slow down) conditions. An insertion warning condition occurs when the system determines that insertion of the stimulating assembly is approaching, or is likely to soon satisfy, one of the insertion stop conditions. For example, an insertion warning condition can be detected by, for example, identifying the start of a rise in, or a steady rise in, the CM magnitude indicating an approach to the peak (for the target stop point) or the start of a drop in the CM magnitude (for the error stop point). In other examples, an insertion warning condition could be detected using the multi-frequency or multi-electrode recording techniques described elsewhere herein. Regardless of how detected, the detection of an insertion warning condition may result in the initiation of a feedback mechanism indicating that insertion of the stimulating assembly into the cochlea should be slowed (e.g., to slow automated forward movement of a stimulating assembly, an alter or notification to a surgeon to slow forward movement, etc.).

In certain embodiments, the target stop point may be refined dynamically during the insertion when, for example, the measured inner ear potentials (measured during insertion) suggest the procedure to be an outlier to that which was originally expected. An example might be a surgery where the insertion reaches beyond the pre-operatively determined stop point and the cochlear microphonic signal is continuing to increase rapidly. Here the surgeon would continue to insert the array past this point until the insertion reaches a revised stop point determined by a slight decrease in the cochlear microphonic.

In one example of FIG. 3, one or more pre-operative measurements (e.g., an audiogram) are performed to determine where the recipient's residual hearing starts. This information is used to set a target location to which a distal end of a stimulating assembly is to be asserted so that the distal end is positioned close to the boundary where the residual hearing begins. While the stimulating assembly is inserted, an acoustic input is delivered to the cochlea and the system measures ECoG responses of the cochlea cells to the acoustic input. These real-time measurements can be utilized to determine when the distal end of the stimulating assembly approaches the target location (target stop point) and/or to determine if the stimulating assembly contacts or otherwise interferes with the basilar membrane during the insertion process. Such an approach marries the functional/behavioral hearing, as indicated by the audiogram, with electrophysiological/objective measurements, as indicated by the ECoG responses, to provide a customizable insertion depth stopping point for each recipient.

In a specific example in accordance with embodiments presented herein, an audiogram is performed on a recipient and indicates that a recipient has useable residual beginning around, and below, approximately 500 Hz. As such, a stimulating assembly should be inserted in this recipient such that the distal end advances close to the 500 Hz region, but not beyond this region. In order words, 500 Hz is entered as the target stop point for insertion of the stimulating assembly.

During insertion, a 500 Hz acoustic signal is delivered to the recipient's cochlea, and a hearing prosthesis performs ECoG measurements via one or more contacts (electrodes) within the cochlea. An intra-operative system monitors the ECoG responses generated from the measurements. As the one or more contacts approach the 500 Hz region of the cochlea, an increase in the EcoG amplitude is detected. The reason for this increase is that the one or more contacts move closer to the point of excitation (i.e., the 500 Hz region). When the one or more contacts reach the 500 Hz region, a peak in the ECoG response amplitude occurs. However, if the one or more contacts move past the region 500 Hz region, the ECoG response amplitude begins to drop. In certain such embodiments, the CM amplitude is utilized, where the CM is a phase following response. However, other EcoG components or attributes, such as the phase, shape of the waveform (morphology), frequency, etc. could be used in alternative embodiments.

Figure 6:
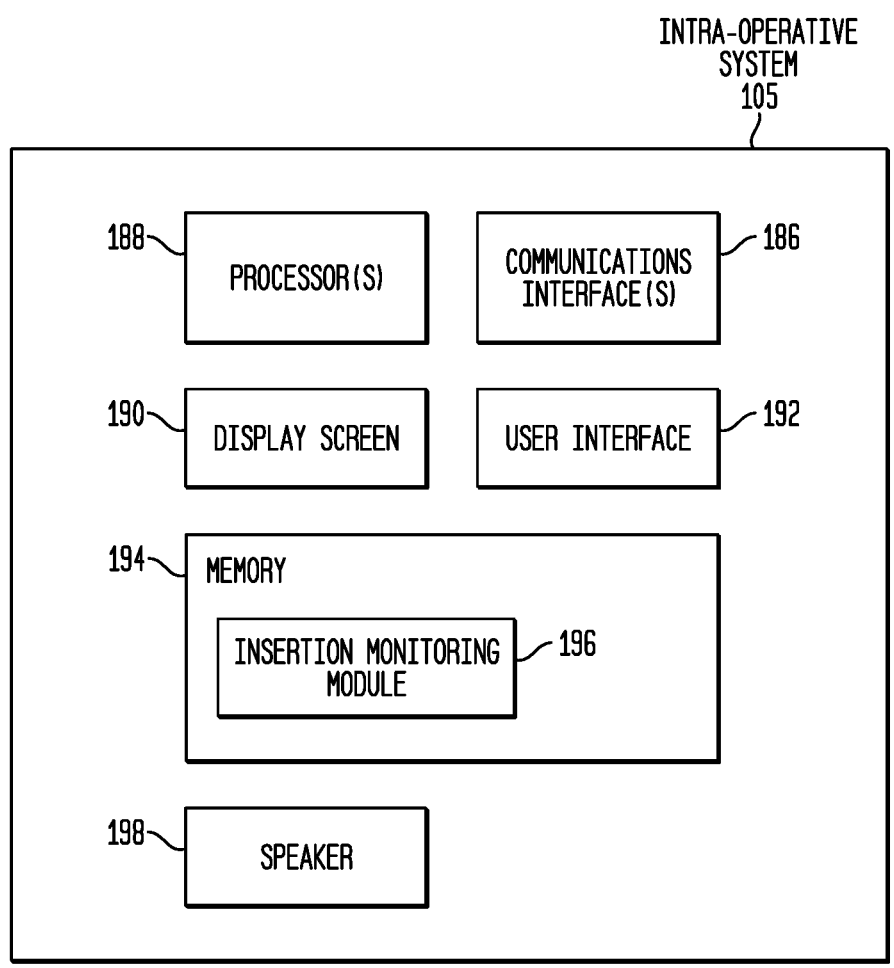
FIG. 6 is a block diagram of an intra-operative system in accordance with embodiments presented herein.

FIG. 6 is block diagram illustrating further details of one arrangement for an intra-operative system, such as system 105, in accordance with embodiments presented herein. As noted above, illustrative intra-operative system 105 may be, for example, a computing device, such as a remote assistant for the hearing prosthesis, computer (e.g., laptop, desktop, tablet), mobile phone, etc., or other device configured for communication with an electro-acoustic hearing prosthesis, such as prosthesis 100 of FIGS. 1A and 1B. In certain embodiments, the intra-operative system 105 may include both a computing device an external component of a hearing prosthesis.

Referring specifically to the arrangement of FIG. 6, the intra-operative system 105 comprises one or more communication interfaces 184, one or more processors 188, a display screen 190, a user interface 192, a memory 194, and a speaker 198. The memory 194 includes insertion monitoring module 196.

The one or more communications interfaces 186 comprise one or more elements for wired or wireless communication with a hearing prosthesis. The communications interfaces 186 may comprise, for example, a short-range wireless transceiver, such as a Bluetooth® transceiver that communicates using short-wavelength Ultra High Frequency (UHF) radio waves in the industrial, scientific and medical (ISM) band from 2.4 to 2.485 gigahertz (GHz). Bluetooth® is a registered trademark owned by the Bluetooth® SIG. The communications interfaces 186 may also or alternatively comprise a telecommunications interface, a wireless local area network interface, one or more network interface ports, a radio-frequency (RF) coil and RF transceiver, etc.

The display screen 190 is an output device, such as a liquid crystal display (LCD), for presentation of visual information to a user (e.g., surgeon). The user interface 192 may take many different forms and may include, for example, a keypad, keyboard, mouse, touchscreen, display screen, etc. In certain embodiments, the display screen 190 and user interface 190 are integrated to form a touch-screen display.

Memory 194 may comprise one or more tangible (non-transitory) computer readable storage media, such as read only memory (ROM), random access memory (RAM), magnetic disk storage media devices, optical storage media devices, flash memory devices, electrical, optical, or other physical/tangible memory storage devices. The one or more processors 188 are, for example, microprocessors or microcontrollers that execute instructions for the insertion monitoring module 196 stored in memory 194. That is, in one form, the insertion monitoring module 196 is implemented as software, sometimes referred to herein as insertion monitoring software, at intra-operative system 105. Therefore, when the insertion monitoring software is executed by the processors 188, the intra-operative system 105 is operable to perform the operations described herein.

Figure 7:
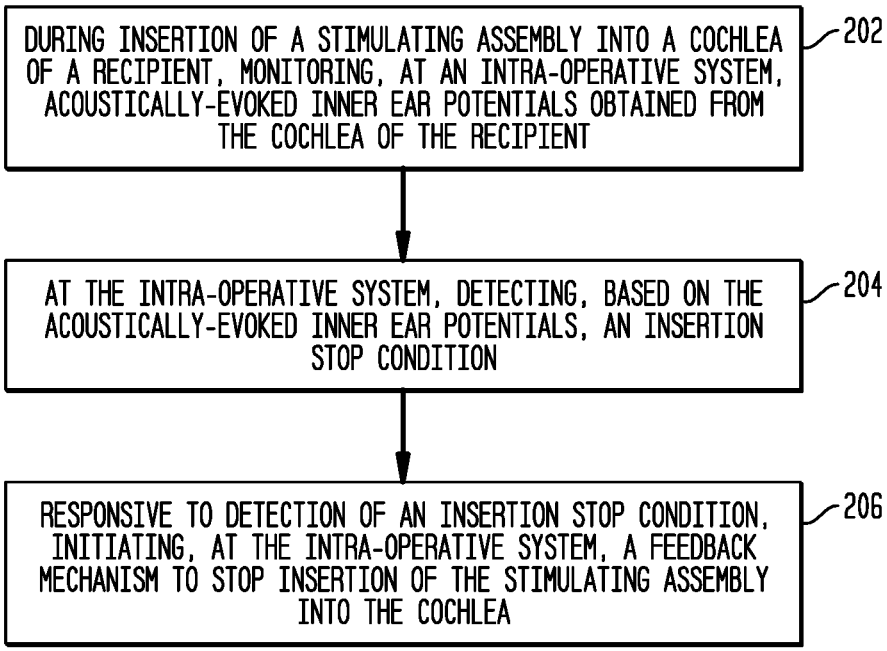
FIG. 7 is a flowchart of another example method in accordance with embodiments presented herein.

FIG. 7 is a flowchart of a method 200 in accordance with embodiments presented herein. Method 200 begins at 202 where, during insertion of a stimulating assembly into a cochlea of a recipient, an intra-operative system monitors acoustically-evoked inner ear potentials obtained from the cochlea of the recipient. At 204, the intra-operative system, detects, based on the acoustically-evoked inner ear potentials, an insertion stop condition. At 206, responsive to detection of an insertion stop condition, the intra-operative system initiates a feedback mechanism to stop insertion of the stimulating assembly into the cochlea.

As noted above, presented herein are techniques for monitoring the insertion of an intra-cochlear stimulating assembly for the occurrence of one or more insertion stop or warning conditions. Also as noted, the insertion monitoring is based on objectively measured inner ear responses/potentials, such as acoustically-evoked potentials. As a result, a feature of the techniques presented herein is an improved ability to preserve the recipient's post-operative residual hearing through the provision of dynamic and static insertion metrics.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
pre-operatively determining an initial insertion stop frequency of a cochlea of a recipient;
inserting a stimulating assembly into the cochlea of the recipient towards the pre-operatively determined initial insertion stop frequency;
during insertion of the stimulating assembly into the cochlea of the recipient, obtaining intra-operative acoustically-evoked inner ear potentials from the cochlea;
analyzing the intra-operative acoustically-evoked inner ear potentials obtained from the cochlea in view of normative data to determine a revised insertion stop frequency;
detecting, based on continued monitoring of the intra-operative acoustically-evoked inner ear potentials, occurrence of an insertion stop condition associated with the revised insertion stop frequency; and
responsive to detection of the occurrence of the insertion stop condition, initiating, at an intra-operative system, a feedback mechanism.

2. The method of claim 1, wherein analyzing the intra-operative acoustically-evoked inner ear potentials obtained from the cochlea in view of normative data to determine the revised insertion stop frequency comprises:
comparing the intra-operative acoustically-evoked inner ear potentials obtained with one or more normative profiles generated based on characteristics of prior insertions in cochleas of other recipients; and
refining the revised insertion stop frequency to account for deviations between the intra-operative acoustically-evoked inner ear potentials obtained from the cochlea and the one or more normative profiles.

3. The method of claim 1, wherein initiating a feedback mechanism to stop insertion of the stimulating assembly comprises:
at least one of slowing, stopping, or modifying automated insertion of the stimulating assembly.

4. The method of claim 1, wherein initiating a feedback mechanism to stop insertion of the stimulating assembly comprises:
generating a notification for a user to at least one of slow, stop, or modify insertion of the stimulating assembly.

5. The method of claim 1, further comprising:
detecting, based on the intra-operative acoustically-evoked inner ear potentials, an insertion warning condition; and
responsive to detection of an insertion warning condition, initiating a feedback mechanism to slow insertion of the stimulating assembly into the cochlea.

6. The method of claim 1, wherein detecting the occurrence of the insertion stop condition comprises:
detecting a relative change in the intra-operative acoustically-evoked inner ear potentials indicating that a one or more stimulating contacts of the stimulating assembly are located at a tonotopic position corresponding to the revised insertion stop frequency.

7. The method of claim 6, wherein detecting a relative change in the intra-operative acoustically-evoked inner ear potentials indicating that a one or more stimulating contacts of the stimulating assembly are located at a tonotopic position corresponding to the revised insertion stop frequency comprises:
detecting a peak or near peak in an attribute of the intra-operative acoustically-evoked inner ear potentials associated with the insertion stop frequency.

8. The method of claim 1, comprising:
prior to insertion of the stimulating assembly, performing one or more pre-operative tests on the cochlea; and
determining the initial insertion stop frequency based on the one or more pre-operative tests.

9. The method of claim 8, wherein performing one or more pre-operative tests on the cochlea comprises:
performing an audiogram measurement of the cochlea to determine at least one of frequency or frequency range where residual hearing begins in the cochlea.

10. The method of claim 1, further comprising:
generating, during insertion of the stimulating assembly, acoustic signals for acoustic stimulation of the cochlea; and
capturing the acoustically-evoked inner ear potentials in response to delivery of the acoustic signals to the cochlea.

11. The method of claim 1, further comprising:
delivering one or more complex acoustic inputs having a plurality of frequencies each associated with a different tonotopic region of the cochlea to the cochlea; and
obtaining the acoustically-evoked inner ear potentials in response to the one or more complex acoustic inputs.

12. The method of claim 1, further comprising:
obtaining the acoustically-evoked inner ear potentials via a plurality of different contacts of the stimulating assembly.

13. The method of claim 1 wherein the pre-operative acoustically-evoked inner ear potentials are evoked using an acoustic input at a number of different frequencies and a fixed presentation level to provide a baseline recording of the inner ear potentials at each of a number of different frequencies.

14. The method of claim 13 further comprising monitoring the relative amplitudes of the inner ear potentials in said baseline recording to indicate a region where maximum amplitudes can be expected at each frequency.

* * * * *